United States Patent
Alitalo et al.

(10) Patent No.: US 10,508,290 B2
(45) Date of Patent: Dec. 17, 2019

(54) MEANS AND METHODS FOR METHANE PRODUCTION

(71) Applicant: QVIDJA KRAFT AB, Helsinki (FI)

(72) Inventors: Anni Alitalo, Espoo (FI); Erkki Aura, Tammela (FI)

(73) Assignee: QVIDJA KRAFT AB, Helsinki (FI)

( * ) Notice: Subject to any disclaimer, the term of this patent is extended or adjusted under 35 U.S.C. 154(b) by 240 days.

(21) Appl. No.: 14/399,410

(22) PCT Filed: May 7, 2013

(86) PCT No.: PCT/FI2013/050503
§ 371 (c)(1),
(2) Date: Nov. 6, 2014

(87) PCT Pub. No.: WO2013/167806
PCT Pub. Date: Nov. 14, 2013

(65) Prior Publication Data
US 2015/0099286 A1 Apr. 9, 2015

(30) Foreign Application Priority Data

May 8, 2012 (FI) ...................................... 20125496

(51) Int. Cl.
*C12P 5/02* (2006.01)
*C12N 11/14* (2006.01)
*C12M 1/107* (2006.01)
*C12M 1/12* (2006.01)
*C12M 1/00* (2006.01)

(52) U.S. Cl.
CPC .............. *C12P 5/023* (2013.01); *C12M 21/04* (2013.01); *C12M 25/16* (2013.01); *C12M 29/00* (2013.01); *C12N 11/14* (2013.01); *Y02E 50/343* (2013.01)

(58) Field of Classification Search
CPC ...... C12M 21/04; C12M 25/16; C12M 29/00; C12N 11/14; C12P 5/023; Y02E 50/343
See application file for complete search history.

(56) References Cited

U.S. PATENT DOCUMENTS

| 4,921,799 A | 5/1990 | Kitaura et al. |
| 2004/0154982 A1 | 8/2004 | Irani |
| 2007/0218540 A1* | 9/2007 | Guiot .................. C02F 1/4676 435/262.5 |

(Continued)

FOREIGN PATENT DOCUMENTS

| CN | 2587875 Y | 11/2003 |
| EP | 1574581 A2 | 9/2005 |

(Continued)

OTHER PUBLICATIONS

Aura, E., "Maan mikrobit tuottamaan hiilidioksidista polttoainetta", In publication Maapera muuttuvassa maailmaasa, V. Maaperatieteiden paivien laajennetut abstraktit. Ed. Soinne, H. et al. Pro Terra, No. 41. pp. 53-54 (2009). http:/www.maapera.fi/ProTerra/Pro%20Terra%2041%202009.pdf.

(Continued)

*Primary Examiner* — William H. Beisner
*Assistant Examiner* — Danielle B Henkel
(74) *Attorney, Agent, or Firm* — FisherBroyles, LLP

(57) ABSTRACT

A solid state fermentation process for producing methane, and a bioreactor and solid support for use in the process are disclosed.

8 Claims, 1 Drawing Sheet

(56) References Cited

U.S. PATENT DOCUMENTS

| | | | | |
|---|---|---|---|---|
| 2010/0233775 A1* | 9/2010 | Schroder | ............... | C12M 21/04 |
| | | | | 435/167 |
| 2011/0281333 A1* | 11/2011 | Brown | .................... | C12N 1/20 |
| | | | | 435/252.1 |
| 2012/0028321 A1* | 2/2012 | Criddle | .................. | C12P 7/625 |
| | | | | 435/146 |

FOREIGN PATENT DOCUMENTS

| EP | 1419234 B1 | 3/2011 |
|---|---|---|
| JP | 5633093 | 4/1981 |
| JP | 57155994 A | 9/1982 |
| JP | 2009045560 | 3/2009 |
| WO | 2011/123854 A3 | 10/2011 |

OTHER PUBLICATIONS

Technical Bulletin ZONOLITE® #3 Agricultural/horticultural Vermiculite, W.R. Grace & Co, Conn, USA http://www.na.graceconstruction.com/vermiculite/download/ZHortAgr_1.pdf., pp. 1, 2, 4, (2000).

Bugante et al., "Methane Production from Hydrogen and Carbon Dioxide and Monoxide in a Column Bioreactor of Theromophilic Methanogens by Gas Recirculation", Journal of Fermentation and Bioengineering, vol. 67, No. 6, pp. 419-421 (1989).

Jee et al., "Continuous CH4 Production from H2 and CO2 by Methanobacterium Thermoautotrophicum in a Fixed-Bed Reactor", J. Ferment. Technol., vol. 66, No. 2, pp. 235-238 (1988).

Auli Rainio, International Search Report for corresponding Finnish Application No. 20125496, pp. 1-2 (dated Aug. 18, 2013).

Auli Rainio, Office Action for corresponding Finnish Application No. 20125496, pp. 1-5 (dated Jan. 18, 2013).

Extended European Search Report, Application No. EP 13 78 8252, 6 pages, dated Feb. 11, 2016.

Office Action for Indian Patent Application No. 10038/DELNP/2014 dated Dec. 12, 2018.

\* cited by examiner

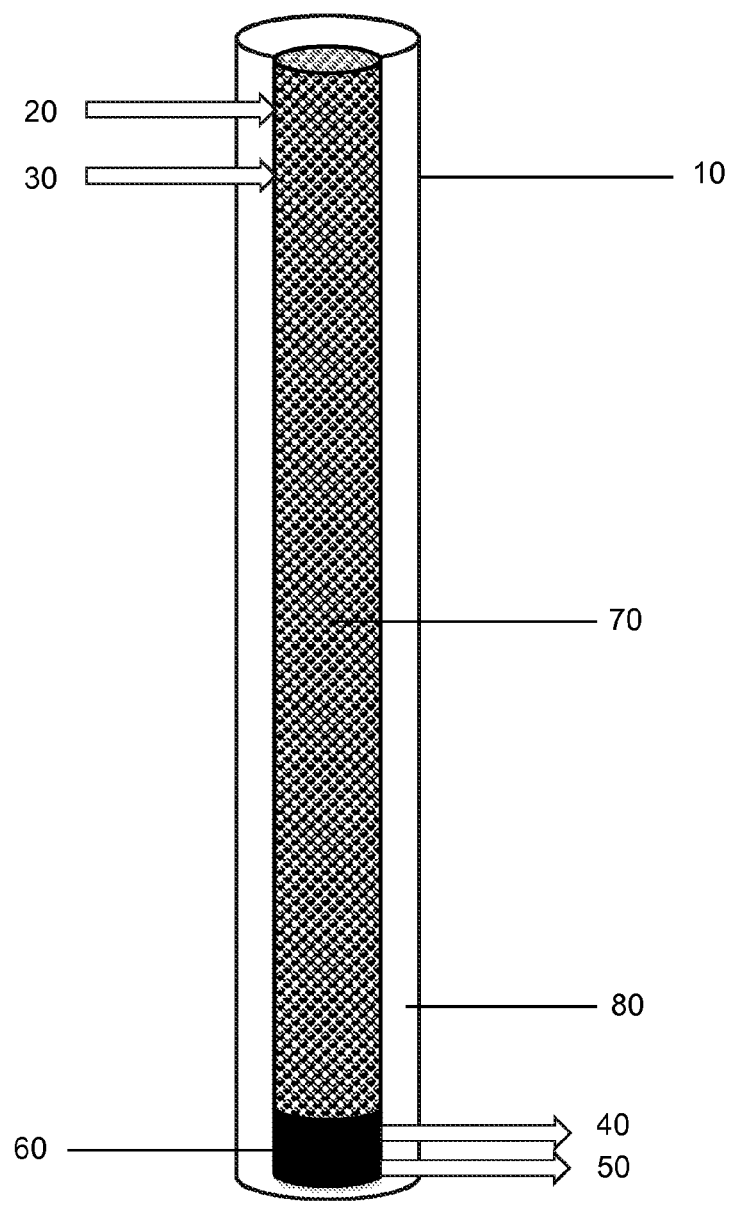

MEANS AND METHODS FOR METHANE PRODUCTION

CROSS-REFERENCE TO RELATED APPLICATIONS

This application is a National Stage application of International Application No. PCT/FI2013/050503, filed May 7, 2013, which claims benefit to Finnish Application No. FI 20125496, filed May 8, 2012, which are incorporated by reference herein in their entirety.

BACKGROUND

Field

The present invention relates to a solid state fermentation process for producing methane, and to a bioreactor and solid support for use in said process.

Description of the Related Art

Methane ($CH_4$) is a simple alkane hydrocarbon and the main component of natural gas. It is an attractive fuel, which fits well to the existing infrastructure. For instance, it may be used directly to heat homes and commercial buildings by feeding into the existing gas network which in many countries has one or two years of gas storage capacity. Methane may also be used in the generation of electric power or as a transportation fuel in gas vehicles.

Methane may be produced by reacting carbon dioxide and hydrogen in a Sabatier reaction: $CO_2+4H_2 \rightarrow CH_4+2H_2O$. The reaction may be catalyzed by two alternative ways: inorganically using metal catalysts at temperatures of several hundred degrees Celsius, or microbiologically at some tens of degrees Celsius.

Owing to the very high operating temperature required and the explosive nature of hydrogen, methane production in inorganic catalysers is a challenging task. Furthermore, required temperature control consumes energy thereby reducing the net efficiency of the system. These drawbacks can be avoided by using microbiologically catalyzed methane fermenting bioreactors.

General environmental factors affecting microbial activity in any bioreactor include water content, temperature, pH, partial pressure of dissolved oxygen and other gases, nutritional conditions, and degree of homogeneity. Traditionally, fermentation processes are carried out either in liquid or on moist solid particles. Mechanical agitation or stirring is the most common way of enhancing the transfer of gases and other substances in the bioreactor. Liquid fermentation coupled with agitation provides bioreactors that are easy to control. However, such bioreactors are expensive and agitation consumes high amounts of energy. If the bioreaction uses gaseous substrates and/or produces gaseous end products, securing efficient gas transfer at low cost becomes extremely difficult. Furthermore, formation of waste water in liquid fermentors may become a particular problem, especially, if the bioreaction produces water.

Solid-state fermentation processes provide several advantages over liquid fermentation processes. For instance, water which is a prerequisite for microbial growth exists mainly as adsorbed into or bound capillarily to the moist solid particles in the solid-state bioreactors. Thus, the water phase in the spaces between the particles is discontinuous and most of the inter-particle space is filled by the gas phase. This makes it relatively easy to feed gaseous starting materials into the bioreactor by applying pressure. In addition, any gaseous end products may exit the system by pressure differences. No agitation is needed in solid-state bioreactors and, thus, instrumentation may be far simpler than in liquid bioreactors. Furthermore, remarkably dense microbial growth on the moist solid particles may be achieved, resulting in high fermentation efficiency. The solid-state approach is particularly suitable for large-scale fermentation processes and bioreactors in cases where the unit prices of the end products are low and, thus, the aim is to build low-cost bioreactors with low maintenance costs.

There are some disadvantages associated with solid-state fermentation, too. For instance, owing to varying physical and chemical environmental conditions, the microbial growth and its efficacy may be unevenly distributed over the solid particles. Since the solid-state bioreactors cannot be homogenized by stirring, the availability of nutrients to the microorganisms may be uneven and it may be difficult to provide pH control. Furthermore, aeration or transfer of gaseous substances between different parts of the bioreactor may be limited. This may, for instance, be due to a blockade of the inter-particle space by condensing water, or water produced in the bioreaction. On the other hand, in cases where the bioreaction does not produce water, the solid particles may desiccate owing to gravity or gas flows, thus lowering the fermentation capacity of the microorganisms.

There have been attempts to produce methane in solid-state bioreactors. For instance, Jee et al. reported in Biotechnology Letters (1988, Vol 10: 243-248) that efficient $CH_4$ production from $H_2$ and $CO_2$ could be achieved by fixing methanogen cells on a solid support such as porous ceramic. However, in long term operation the accumulation of methanogen cells on the support hindered the homogeneous flow of the gaseous substrates through the pores of the support and this caused a gradual decrease of methanation from $H_2$ and $CO_2$.

The present invention aims at avoiding disadvantages of conventional solid-state bioreactors, especially when the bioreaction involves gaseous starting materials and/or reaction products, and low building and maintenance costs are desired.

SUMMARY

One aspect of the present invention relates to a bioreactor comprising a $CO_2$ distribution system, an $H_2$ distribution system, a water collection system, and a $CH_4$ collection system, wherein the bioreactor is loaded with a porous solid support in which at least 10% of the pore volume have a size resulting in a water suction of about 0.01 to about 1.0 bar as compared to free water, and wherein the solid support is inoculated with methanogens, and the bioreactor comprises a solid phase, a liquid phase and a gaseous phase, wherein the volume of the gaseous phase is 20% to 80% of the volume of the bioreactor.

Another aspect of the invention relates to process for generating methane by solid state fermentation, comprising the steps of a) providing the a bioreactor according to any embodiment of the present invention, b) feeding $CO_2$ and $H_2$ into the reactor, c) anaerobically bioconverting said $CO_2$ and $H_2$ into methane and water, and d) collecting methane from the bioreactor.

Still another aspect of the invention relates to the use of a solid support comprising (i) particles having a diameter of 0.1 mm to 10 mm for at least 20% of the particles; (ii) a spongy structure material having a pore size of 0.1 mm to 10 mm for at least 10% of its pores; or (iii) a filamentous structurematerial, wherein the diameter of inter-filamentous spaces is from 0.1 mm to 10 mm for at least 10% of its inter-filamentous spaces; or a mixture thereof, for generating methane from carbon dioxide and hydrogen in a solid state fermentation process. Specific embodiments of the invention are set forth in the dependent claims. Other aspects, details, embodiments and advantages of the present invention will become apparent from the following drawings, detailed description and examples.

BRIEF DESCRIPTION OF THE DRAWINGS

In the following the invention will be described in greater detail by means of preferred embodiments with reference to the attached drawings, in which FIG. 1 shows a schematic representation of an exemplary methane bioreactor.

DETAILED DESCRIPTION

The present invention relates to a solid state fermentation (SSF) process and a bioreactor, wherein carbon dioxide ($CO_2$) and hydrogen ($H_2$) are converted into methane ($CH_4$) and water by methanogens grown on a porous solid support.

As used herein, the term "methanogen" refers to an anaerobic microorganism belonging to the domain Archaea and capable of producing methane as a metabolic by-product. Methanogens may also be referred to as methanogenic microorganisms. Non-limiting examples of methanogens suitable for use in the present invention include species belonging to the genus *Methanobacterium*, such as *M. formicicum, M, defluvii, M. oryzae, M. palustre, M. subterraneum*, and *M. thermoflexum*. Herein, methanogens may be used in any desired mixture or combination, or as a pure culture of a single methanogenic species.

Methanogens may be obtained from culture collections or isolated, for instance, from swamps, such as peat bogs or sphagnum bogs, or other wetlands. The choice of the methanogen in the present process may depend on various factors including, but not limited to, nutrient, temperature, and pH requirements of a given methanogen as readily understood by a skilled person. In some embodiments, it may be advantageous to utilize methanogens derived from Nordic nature owing to their favourable temperature requirements. In other words, such methanogens work well in lower temperatures and, thus, less energy is needed for heating the bioreaction.

The bioreactor according to the present invention comprises three major phases, i.e. a solid phase comprising the porous solid support, a liquid phase comprising water produced in the fermentation process, and a gaseous phase comprising $CO_2$, $H_2$, and $CH_4$. The volume of the gaseous phase should be 20% to 80% of the volume of the bioreactor in order to achieve a large enough liquid-solid interface. Furthermore, the greater the gaseous phase, the longer the reaction time and, thus, the more efficient the bioreactor. It is important that the solid phase is distributed evenly in the dispersing gaseous phase throughout the bioreactor.

Capillary conductivity and sufficient inter-solid-support gas volume define the gas and liquid flow characteristics through the solid support. Adequate capillary conductivity is required to ensure that the gas and liquid transfer can be maintained at the desired levels for the duration of the fermentation process. Furthermore, humidity in the bioreactor must be high enough to enable the methanogens to grow on the solid support. On the other hand, too high moisture content would be harmful to at least some types of methanogens, as well as block the gas transfer by filling the inter-solid-support space.

Solid support suitable for use in the present invention must be porous in order to obtain sufficient fermentation conditions as described herein. Water binds to the pores of the solid support by capillary forces resulting from adsorption and surface tension. Intensity of the binding may be expressed by pressure units, such as bars. A given pore size corresponds to a certain binding intensity. Assuming that the pores are cylindrical tubes, the radius of the largest pores filled with water may be calculated from the following equation:

$$r=2\gamma/hpg,$$

wherein r is the radius of the pore (m);
$\gamma$ is the surface tension of water, i.e. 0.073 N/m;
h is the water suction expressed as the height of the water column (m) (the absolute value of capillary potential of water);
$\rho$ is the density of water, i.e. 1000 kg/m$^3$;
g is gravitational acceleration, i.e. 9.81 m /s$^2$.
This equation is often presented in a simplified form:

$$D=0.3/h,$$

wherein D is the diameter of the pore (cm); and
h is the water suction expressed as the height of the water column (cm) (the absolute value of capillary potential of water).

The solid support suitable for use in the present invention should be such that at least 10% of the pore volumes have pore diameters resulting in a water suction of about 0.01 to about 1.0 bar as compared to free water. In some embodiments, the solid support may comprise or be in the form of particles having a diameter of 0.1 mm to 10 mm. Any one particle size within this range or any combination thereof may be used in the present process and the bioreactor. Non-limiting examples of suitable average diameters of the pores lie within the range of about 10 nm to about 100 nm, and suitable particle materials include, but are not limited to, material mixtures comprising vermiculite, modified vermiculites, vermiculite-like materials, or synthetic vermiculites; synthetic cation-exchange resins; various peat types; other organic materials; and mixtures thereof as long as they have or they provide the required physical and chemical characteristics described herein. It is particularly important that the solid support provides a gaseous phase, the volume of which is 20% to 80% of the volume of the bioreactor, and which is distributed evenly throughout the bioreactor. In some other embodiments the solid support may comprise or be in the form of a spongy structure having a pore size distribution within the range of about 0.1 mm to about 10 mm for at least 10% of its pore volumes. Non-limiting examples of suitable spongy materials include synthetic spongy materials, such as foamed plastic polymers, as well as natural sponges.

In some yet other embodiments, the solid support may be provided as a filamentous structure. In such cases, inter-filamentous spaces may be regarded as the pores of the filamentous solid support, and their diameter distribution should lie within the range of about 0.1 mm to about 10 mm for at least 10% of the inter-filamentous spaces.

A non-limiting example of a suitable filamentous material includes steel wool. As steel wool does not have any cation-exchange properties it may be provided in a mixture with particles having sufficient cation-exchange properties. Alternatively or in addition, steel wool may be coated or applied with an organic material, such as polyacrylamide, in order to achieve sufficient cation-exchange properties.

The porous solid support may also be any admixture of particles, spongy materials and filaments as long as it fulfils the physical requirements set forth herein.

The porosity of the solid support not only affects the moisture conditions in the bioreactor but also provides a large attachment surface for methanogens and protects them from flushing. In addition, porosity increases the specific surface area of the solid support. In some embodiments, the specific surface area of the solid support is at least 5 $m^2/g$.

High specific surface area, in turn, results in high ion-exchange capacity of the porous solid support. In order to be suitable for use in the present fermentation process, the solid support should have high cationic exchange capacity, typically higher than 0.1 mmol/g. Since most nutrient substances are cationic, cation-exchange properties of the solid support are more important than anion-exchange properties. However, in some embodiments, the solid support may also possess anion-exchange properties. In some further embodiments, the cation-exchange capacity and the anion-exchange capacity may even be almost equal to each other.

Furthermore, high specific surface area together with high cation-exchange capacity results in formation of a biofilm. This, in turn, increases the efficiency of the fermentation process due to high methanogen content.

The above-mentioned properties of the solid support provide sufficient buffering properties in the fermentation process. When the solid support, owing to its cation-exchange capacity, is capable of exchanging hydrogen and/or hydroxyl ions with a liquid phase, there should be no need for additional pH controlling.

Solid supports not suitable for use in the present invention include materials that are inactive in terms of their cation exchange capacity. More specific examples of such materials include silica-based materials, wood-based materials, most plastics (unless they are couples with active groups), and most stone materials, such as feldspar and quartz. It is noteworthy that although vermiculite exists in forms having a sufficient cation exchange capacity, it is not a suitable solid support material to be used alone in the present bioreactor. This is because it is not possible to achieve a sufficient gaseous phase volume with sole vermiculite. Spontaneous compaction through wetting and drying effect would reduce the gaseous phase volume below 20% of the volume of the bioreactor even if in some specific cases it might be possible to achieve an initial gaseous phase volume of slightly over 20% of the volume of the bioreactor. Thus, if vermiculite is to be employed in the present bioreactor, it needs to be provided in a mixture with other, non-flat materials, such as perlite, in order to fulfil the requirement that the volume of the gaseous phase must be 20% to 80% of the volume of the bioreactor.

The present process may be carried out in a bioreactor which is, for instance, a glass, stainless steel, or plastic tank or vessel. The material of the bioreactor should be non-toxic to the methanogens used in the process. The size and shape of the bioreactor may vary within a range known to a person skilled in the art depending on different parameters, such as the choice of the solid support material. Preferably, the size is suitable for industrial scale methane production. The bioreactor should be low-cost, easy to operate, and reliable.

An exemplary bioreactor is illustrated in FIG. 1. The upper end of the bioreactor vessel 10 is provided with a $CO_2$ distribution system 20 and a hydrogen distribution system 30 whereas the lower end of the vessel 10 is provided with a water collection system 40 and a $CH_4$ collection system 50. The bottom part of the bioreactor vessel is covered with a layer of crushed limestone 60, while the remainder of the vessel is loaded with a porous solid support material 70 described herein. The bioreactor vessel is surrounded by a heating water circulation 80.

The bioreactor may be provided with various sensors for monitoring desired parameters such as the temperature, pH, and humidity in the reactor. Such sensors are readily available in the art. The bioreactor may also be provided with a gas analyser for monitoring the operation of the bioreactor and the yield of methane production.

Temperature control of the present process may be obtained e.g. by connecting a closed water circulation system to the bioreactor. Such a system may provide either heating or cooling of the process depending on the needs of a given methanogen. Heat is transferred between the water circulation system and the bioreactor by conductivity. Other means and methods for adjusting the temperature of the present process are well known in the art.

Carbon dioxide used as a starting material in the present fermentation process may be captured from any suitable source including, but not limited to combustion of fossil fuels such as coal, oil or gas in power plants, and industrial facilities where carbon dioxide is produced as a by-product of various non-energy related activities.

Hydrogen used as the other starting material in the present process may be obtained from various sources. Another non-limiting way of obtaining high-purity hydrogen is through electrolysis of water into its components, oxygen and hydrogen. Energy required for the reforming process and electrolysis may be obtained, for instance, from renewable energy sources such as solar, water, or wind power. Means and methods for producing hydrogen are well known in the art.

In one embodiment, the bioreactor is provided with a hydrogen cell, such as a solid oxide electrolysis cell (SOEC). Such cells are commercially available or may be constructed as known in the art.

Distribution systems for carbon dioxide and hydrogen may be separate or combined, as desired. However, it may be advantageous to mix these gases prior to feeding into the bioreactor in order to avoid any danger of hydrogen explosion.

The fermentation process is carried out under conventional conditions used for culturing methanogens, i.e. it is carried out under anaerobic conditions. Oxygen may be purged from the reactor by sweeping or purging with a non-oxygenated gas such as nitrogen, carbon dioxide, hydrogen or any other anaerobic environment supporting gas.

Many methanogens require additional nutrients such as nitrogen, nickel, and/or cobalt for their growth. These substances may be supplied during the fermentation process or, preferably, provided attached to a solid support having cation-exchange capacity as described above thus resulting in a self-sustained process in this respect. Nitrogen may be given e.g. in the form of urea or ammonium carbonate. In some embodiments, wood ash may be used to provide additional nutrients to the methanogens. The specific concentration on these elements depends on the micro-organism being used.

In some embodiments, efficiency of the fermentation process may be boosted by addition of sodium bicarbonate.

A functional bioreactor and methane fermentation process according to the present embodiments may be set up in a short period of time, such as a couple of days. After the fermentation process is up and running, the bioreactor will continue to produce methane and water for a period of several months or years. In some embodiments, the efficiency of the bioreaction may exceed several watts per litre and/or the purity of methane produced may be as high as at least 95%. The more efficient the bioreactor by volume, the smaller its size may be. Methane collected from the bioreactor may be used for any desired purpose including, but not limited to, protein production as described in European Patent No. 1419234B. If desired, it may also be fed directly to a gas-fired electric power generator to be transformed into electrical energy, piped into homes for domestic heating and cooking purposes, used as a raw material in chemical industry, or it may be used as a transportation fuel. If desired, methane may be liquefied to enable easy and cost-efficient transit to markets, where it is regasified prior to use. It will be obvious to a person skilled in the art that, as the technology advances, the inventive concept can be implemented in various ways. The invention and its embodiments are not limited to the examples described below but may vary within the scope of the claims.

EXAMPLE 1

A 4.4 litre vertical bioreactor illustrated in FIG. 1 was constructed from a polypropylene sewer pipe having a diameter of 75 mm and height of 1000 mm. A nylon inlet tube for $CO_2$ and $H_2$ delivery was fitted to the upper part of the pipe. The lower part of the pipe was provided with two outlet tubes, one for gas collection and the other for possible maintenance procedures such as water recycling. The lower part of the sewer pipe was covered with a 10 cm thick layer of crushed limestone and the rest of the bioreactor was filled with a solid support, vermiculite. Prior to the filling, 2 kg of vermiculite was mixed with 200 g of perlite, 26.3 g of wood ash, 0.5 g of hydrated cobalt sulphate ($CoSO_4.7H_2O$), and 0.5 g of hydrated nickel chloride ($NiCl_2.6H_2O$). The bioreactor was inoculated with a 2 litre aqueous slurry of methanogens obtained from an earlier bioreactor and stored in a mixture of $CO_2$ and $H_2$ by pumping through the inlet of the upper part of the bioreactor.

A water circulation system was used for heating the bioreactor. The temperature of the heating water was adjusted to a desired level, typically 52.3 to 54.8° C.

Hydrogen and $CO_2$ mixed in the collection tank were conveyed to the bioreactor through the nylon inlet tube fitted to the upper part of the bioreactor. The proportion and mode of $H_2$ delivery was adjusted at the beginning of the fermentation process on the basis of variables such as dryness of the bioreactor.

Gases exiting the bioreactor ($CH_4$ and $CO_2$) were analysed with a gas analyser (Dräger GasVisi, X-am 7000).

When the rate of $H_2$ feeding varied between 20.1 litre/day and 30.1 litre/day, the average efficiency of the bioreactor varied between 0.7 watt/litre and 1.01 watt/litre, while the methane yield varied between 60.66 Vol % and 72.60 Vol %.

EXAMPLE 2.

Further tests revealed that increasing the volume of the gaseous phase in the bioreactor to 20% to 80% boosted the efficiency of the bioreactor significantly.

In an exemplary test, a bioreactor was built as described in Example 1 with the exception that one fourth of vermiculite was replaced with perlite. This structural modification resulted in a gaseous phase volume of over 20% of the volume of the bioreactor. Consequently, the average efficiency of the bioreactor was increased over four fold to 4 watt/litre.

What is claimed is:

1. A solid-state fermentation bioreactor comprising:
    an inlet for $CO_2$ distribution;
    an inlet for $H_2$ distribution;
    an outlet for water collection;
    an outlet for $CH_4$ collection; and
    a porous solid support having interstitial spaces, the porous solid support loaded into the solid-state fermentation bioreactor, wherein at least 10% of the pore volumes have a size resulting in a water suction of about 0.01 to about 1.0 bar as compared to free water, the solid support being inoculated with methanogens, the solid-state fermentation bioreactor comprising a solid phase, a liquid phase and a gaseous phase, wherein the liquid phase is discontinuous in the interstitial spaces, wherein the solid phase is distributed in the gaseous phase, and wherein the volume of the gaseous phase is 20% to 80% of the volume of the bioreactor, and wherein the porous solid support has a cation exchange capacity;
    provided that vermiculite is not used alone as a solid support.

2. The solid-state fermentation bioreactor according to claim 1, wherein said porous solid support comprises:
    particles having a diameter of 0.1 mm to 10 mm for at least 20% of the particles;
    a spongy material having a pore size of 0.1 mm to 10 mm for at least 10% of its pores;
    a filamentous material, wherein the diameter of inter-filamentous spaces is from 0.1 mm to 10 mm for at least 10% of its inter-filamentous spaces; or
    a mixture thereof.

3. The solid-state fermentation bioreactor according to claim 1, wherein said solid support has the cation exchange capacity of at least 0.1 mmol/g.

4. The solid-state fermentation bioreactor according to claim 1, wherein said porous solid support has a specific surface area of at least 5 m²/g.

5. The solid-state fermentation bioreactor according to claim 1, wherein said porous solid support comprises particles having a diameter of 0.1 mm to 10 mm for at least 20% of the particles, and wherein said porous solid support particles are selected from the group consisting of material mixtures comprising vermiculite, material mixtures comprising modified vermiculite, material mixtures comprising vermiculite-like material, material mixtures comprising synthetic vermiculites, synthetic cation exchange resins, various peat types, and mixtures thereof.

6. The solid-state fermentation bioreactor according to claim 1, wherein said porous solid support comprises a spongy material having a pore size of 0.1 mm to 10 mm for at least 10% of its pores, wherein said spongy material is selected from the group consisting of synthetic spongy materials and natural sponges.

7. The solid-state fermentation bioreactor according to claim 1, wherein said porous solid support comprises a filamentous material, wherein the diameter of inter-filamentous spaces is from 0.1 mm to 10 mm for at least 10% of its inter-filamentous spaces, and wherein said filamentous material is coated or non-coated steel wool.

8. A process for generating methane by solid state fermentation, comprising:
    providing a solid-state fermentation bioreactor, the solid-state fermentation bioreactor comprising:
    a $CO_2$ distribution system;
    an $H_2$ distribution system;
    a water collection system;
    a $CH_4$ collection system and a porous solid support having interstitial spaces, the porous solid support loaded into the solid-state fermentation bioreactor, wherein at least 10% of the pore volumes have a size resulting in a water suction of about 0.01 to about 1.0 bar as compared to free water, the solid support being inoculated with methanogens, the bioreactor comprising a solid phase, a liquid phase and a gaseous phase, wherein the liquid phase is discontinuous in the interstitial spaces, wherein the solid phase is distributed in the gaseous phase, and wherein the volume of the gaseous phase is 20% to 80% of the volume of the bioreactor, and wherein the porous solid support has a cation exchange capacity;

feeding $CO_2$ and $H_2$ into the solid-state fermentation bioreactor;

anaerobically bioconverting said $CO_2$ and $H_2$ into methane and water; and collecting methane from the bioreactor.

\* \* \* \* \*